United States Patent [19]

Porsch et al.

[11] Patent Number: 4,752,391
[45] Date of Patent: Jun. 21, 1988

[54] COLUMN FOR PREPARATIVE LIQUID CHROMATOGRAPHY

[75] Inventors: Bedrich Porsch; Jaroslav Voslár; Jaroslav Rosol; Vladimír Kubánek, all of Prague, Czechoslovakia

[73] Assignee: Ceskoslovenska akademie ved, Czechoslovakia

[21] Appl. No.: 86,966

[22] Filed: Aug. 19, 1987

[30] Foreign Application Priority Data

Aug. 21, 1986 [CS] Czechoslovakia .................... 6128-86

[51] Int. Cl.⁴ .............................................. B01D 15/08
[52] U.S. Cl. .................................... 210/198.2; 55/386
[58] Field of Search .............. 210/656, 657, 658, 659, 210/198.2, 198.3; 55/67, 386; 422/70

[56] References Cited

U.S. PATENT DOCUMENTS

| | | | |
|---|---|---|---|
| 3,346,486 | 10/1967 | Winter | 210/198.2 |
| 3,474,908 | 10/1969 | Catravas | 210/198.2 |
| 4,453,954 | 6/1984 | Kolb | 210/198.2 |
| 4,563,276 | 1/1986 | Clark | 210/198.2 |
| 4,636,315 | 1/1987 | Allen | 210/198.2 |

Primary Examiner—Ernest G. Therkorn
Attorney, Agent, or Firm—Leydig, Voit & Mayer

[57] ABSTRACT

A column for preparative liquid chomatography is provided with an inlet tube (5) for injected sample, which is closed on the end with a gauze or fritted plate (6), passes through the center of a lower terminal (3), and ends in the distance equal to 70 to 90% of the total length of the column from the lower end of this tube, whereas the lower terminal (3) has at least four openings (7) or a circular slot or two half-slots which are placed outside the center of terminal on a concentric circle with diameter ranging between 40 to 70% of the inner diameter of column tube (1). The column operates in such a way, that mobile phase is introduced into the column through the center of the upper terminal (2) and a sample is injected into a sorbent through the inlet tube (5) for sample after stopping the flow of mobile phase and then the flow of mobile phase is restored.

1 Claim, 2 Drawing Sheets

COLUMN FOR PREPARATIVE LIQUID CHROMATOGRAPHY

BACKGROUND OF THE INVENTION

The invention pertains to a column for preparative liquid chromatography.

Rapid development of the analytical high-pressure liquid chromatography leading to columns with high separation efficiencies increased the interest in the preparative columns with similar properties. The reason is that the use of smaller particles of a sorbent enables, similarly as in the analytical columns, to increase the efficiency of columns substantially (as much as by an order of magnitude), provided the sorbent is sufficiently rigid in order to withstand the required pressure gradient. Among basic problems which need to be solved in designing the preparative column there are the distribution of mobile phase and injected sample into the column head and the outlet of sample from the column which have to be arranged in a way preventing from an additional spreading of the sample zone and thus from the decrease in efficiency. A considerable spreading of thein jected sample occurs always if a void of space is formed in the column head where the sample is mixed with mobile phase; rinsing of this void leads to rather asymmetric zones of sample. The void may arise, for example, by squeezing the sorbent as a consequence of pressure gradient in chromatography or by a slow dissolution of sorbent particles in mobile phase. All given problems become the more evident the larger is the diameter of column. The inlet and outlet of mobile phase and sample are mostly realized as a central inlet and outlet of the column. They are described columns with a conical shape of the inlet and outlet parts and also columns with complex distributors in the inlet and outlet parts which should secure an uniform distribution and collection of a sample from the whole cross-section of column (for example, Coq B., Cretier G., Rocca J. L.; Journal of Chromatography 186, 457 (1979)). The solutions with the inlet of sample into the column head reliably work provided that a void of space is not formed in the column head. The squeezing of sorbent bed, above all in columns with a large diameter, occurs even with such rigid particles as is the microparticular silica gel. Packing procedures commonly used for analytical columns, which secure the enhanced stability of sorbent bed, i.e. the packing with a suspension of particles at the pressure up to 50–60 MPa, can be applied for preparative columns with difficulty. Thus, formation of such pressure gradient in a column with diameter of 100 mm would require a very complicated packing equipment, a pump in particular. Because operation pressures in the column are lower by an order of magnitude than the above pressure, at least ten times higher pressure resistance of the preparative column would be required in comparison to operation conditions. The tendency is therefore to pack the columns with large diameters by a simple sedimentation in gravitation field. This can be easily achieved, but without a sufficient guaranty that the packing of particles is stable enough under the pressure gradient during operation of the column and the risk of formation of voids in the column head is further increased. Three solutions of this problem are known. The first solution are columns with a sliding piston; the column head, namely its lower part, is formed by a sliding piston which may be slided in such a way that it always presses on the column of sorbent and, at the same time, introduces the sample into sorbent or leads the sample from the sorbent using a suitable distributor, if need be, e.g. in the German Patent Application (FRG) No. 3,021,366 or European Patent Application No. 0040,663. An disadvantage is here the complexity of piston as such and high requirements on the quality of tubes for columns, because the piston must be perfectly sealed against the outer overpressure. Besides, a considerable force has to be developed for shifting the piston in order to compensate the inner overpressure and this force increases with the incrasing diameter. The second possibility consists in manufacturing the column from an elastic material and stabilizing the sorbent column by a radial compression in such a way that a void of space cannot occur (e.g. German Patent Application (FRG) NO. 3,000,475). This solution requires a relatively complex equipment compressing the elastic column and does not completely solve the problem with dissolution of the sorbent and formation of voids during column operation, which problem rapidly grows with the increasing diameter of column, and therefore it is used only for columns with a smaller diameter. The third solution is injection of a sample directly into the sorbent bed on the column head either axially (Katz E., Scott R. P. W.; J. Chromatography 246, 191 (1982)) or from the side of column (Molnar I., Huhn A., Lamer W.; International Laboratory 14, no. 3, 10 (1984)). Equipments of this type are again complicated and sensitive to handling and the sample inlets become often choked. In addition, they always need to use two pumps, one of which leads a mobile phase to the column head while the other leads the sample and mobile phase into the sorbent. If a high efficiency wants to be achieved, the proper setting of both flow rates makes a great difference. The described inlets of sample into the sorbent have been used only in analytical columns. They can be obviously used also for columns with larger diameters, but their complexity would further increase.

SUMMARY OF THE INVENTION

These disadvantages are overcome in a column according to the invention, which consists of a tube with cylindric shape packed with a sorbent and provided on ends with terminals which seal the column against outer overpressure and in which are attached bolts fixing the terminals on the ends of tube, wherein an inlet tube for injected sample, which is closed at the end with a gauze or fritted plate, passes through the centre of the lower terminal and ends in the distance from the lower end of the column equal to 70 to 90% of the total length of tube, whereas the lower terminal has at least four openings or a circular slot or two half-slots furnished with gauzes or fritted plates and these openings or slots are placed outside the centre of the lower terminal on a concentric circle with diameter ranging between 40 and 70% of the inner diameter of the cylindric tube.

An important feature of the invention is the arrangement of inlets of the sample and mobile phase into the column, according to which the mobile phase is introduced through the upper terminal axially and the sample is injected into the sorbent through an inlet tube for sample after stopping the flow of mobile phase and then the flow of mobile phase is restored.

BRIEF DESCRIPTION OF THE DRAWINGS

A diagrammatic assembly of the column according to the invention is displayed in a drawing, where.

DESCRIPTION OF THE PREFERRED EMBODIMENTS

Figure 1:
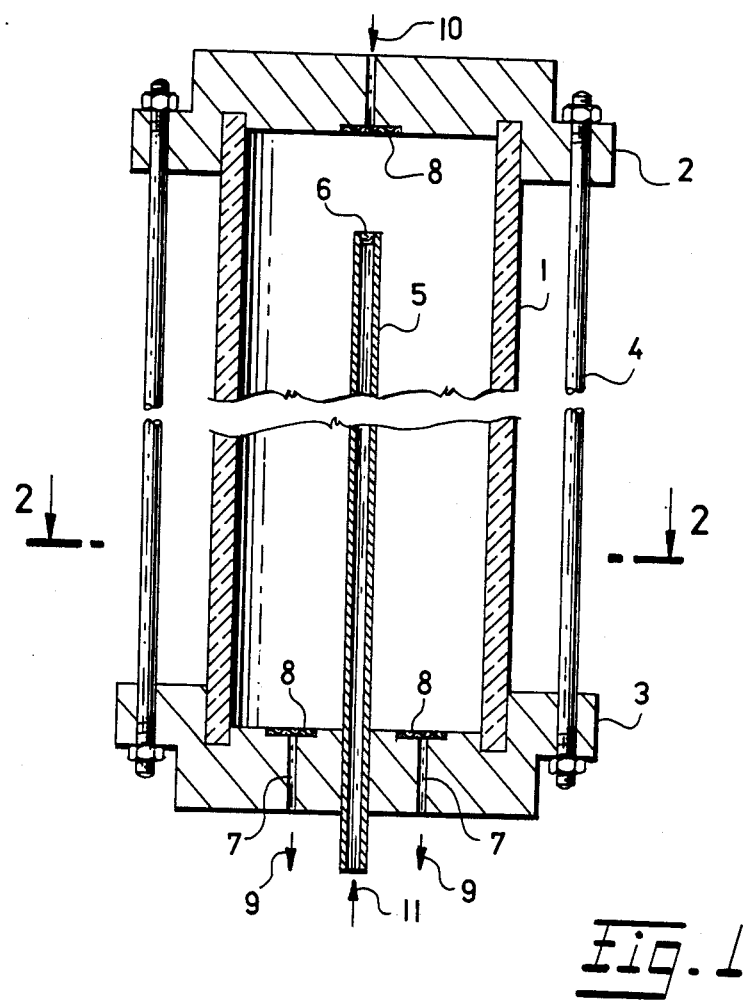
FIG. 1 shows the column in a sectional view and FIG. 2 is a plan central section A—A'.

FIG. 1 shows the column consisting of a tube 1 with cylindric shape which is provided at ends with an upper terminal 2 and a lower terminal 3. The inlet of mobile phase formed by an inlet capillary 10 and provided with a gauze 8 passes through the centre of upper terminal 2. An inlet tube 5 for the injected sample provided at the end with a gauze or fritted plate 6 and connected with an inlet capillary 11 for the sample passes through the centre of the lower terminal 3; four openings 7 furnished with gauzes 8 and leading the mobile phase out through an outlet capillary 9 are performed in the lower terminal 3 and placed on a concentric circle in a half of the inner diameter of tube 1. The upper terminal 2 and the lower terminal 3 are fixed at the ends of tube 1 with bolts 4.

Figure 2:
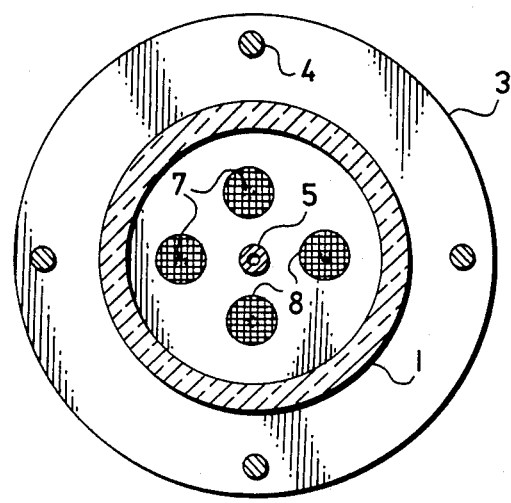

FIG. 2 shows a column consisting of the tube 1 provided at both ends with the upper terminal 2 and the lower terminal 3. The tube 1 is sealed in the upper terminal with a polytetrafluoroethylene sealing ring 12, stainless-steel sealing ring 13 and polytetrafluoroethylene sealing piece 14. The lower part of the upper terminal 2 and its upper part are tighten with bolts 17. The inlet capillary 10 of mobile phase passes through the centre of sealing piece 14 and is sealed with a polytetrafluoroethylene cone 18 and a bored screw 19. An inlet tube 5 is sealed in the lower terminal 3 with the polytetrafluoroethylene sealing ring 12 and the stainless-steel sealing ring 13 in the same way as it is in the upper terminal, and with a polytetrafluoroethylene sealing piece 20 is provided with openings 7 which are covered with gauzes 8. The channels of openings 7 are formed in the upper part 21 of the lower terminal 3 under a stopper 22 and an outlet capillary 9 of mobile phase is sealed with the polytetrafluoroethylene cone 18 and the screw 19. The inlet tube 5 of sample is furnished with a fritted plate 6, screwed into the upper part 21 of the lower terminal 3 and sealed with the polytetrafluoroethylene cone 18 and the screw 19. The inlet tube 5 of sample is tighten from the inner side with a nut 23 with a washer 24. The lower part of the lower terminal 3 and the upper part 21 of this terminal are tightened with bolts 17. The upper terminal 2 and the lower terminal 3 are fixed at the end of tube 1 with bolts 4 which are tighten with nuts 25.

The cylindric tube 1 forming the column may be made from glass, stainless steel, or other material, according to the requirements on its strength and resistance to corrosion, and its diameter is given by the required separation capacity and its value is not limited.

The terminal may have a arbitrary design. The sealing according to the Czechoslovak Pat. No. 236,184 can be advantageously used because it allows to utilize the strength of glass approaching theoretical values, is sufficiently simple, and does not require the tube of special quality with respect to its roundness and the quality of surface.

The openings 7 in the lower terminal 3 serve as outlets for mobile phase. Connection channels for the outlet of mobile phase can be provided in the lower terminal 3 so that the mobile phase leaves the column through a single tube. Also separate tubes may be used which are connected first behind the column.

A standard six-way valve may be advantageously employed for introduction of the sample, because it enables to switch over the flow of mobile phase outside the column and, at the same time, to attach an injection branch and to close the column head without stopping a pump. The valve is switched back after injection and thus the flow of mobile phase is restored.

The column according to the invention has numerous advantages if combined with the described method of sample inlet. The column may be readily packed with a sorbent by a simple sedimentation in gravitation field in such a way, that a tube identical with the tube 1 forming the column is used and both are connected by means of a rubber coupling. Because the inlet tube of sample is placed from below, a complicated introduction of an injection system into the sorbent can be omitted. A sorbent layer above the end of the inlet tube 5 of sample practically replaces a piston for compression of the sorbent as a consequence of a pressure gradient determined by a height of this layer, column diameter, flow rate and viscosity of mobile phase, and the particle size of the sorbent. If need be, this layer can be filled up or replaced again by a simple sedimentation without influencing the efficiency of column. This is important above all in cases when the sorbent may be slightly dissolved by mobile phase as this layer substitutes a saturation column in such a case. In addition, this layer also traps contingent impurities from the mobile phase, which fact has again an importance in the application of columns with large diameters which operate with tens and even with hundreds liters of mobile phase and thus the general requirements on the purity of chromatographic mobile phases may be reduced. If glass tubes are used, the contamination which is often accompanied with a change of sorbent colour may be followed by eye and the sorbent can be readily changed.

Because the openings 7 leading the mobile phase out are placed outside the centre of the lower terminal 3, a substantially better elution of the sample zone occurs from the column circumference and symmetric peaks are obtained even with considerable amounts of the separated sample.

There is no need to work with two pumps if the described method of sample injection is used. In order to connect two columns according to the invention in a series, the inlet on the head of second column can be joint with the outlet from the first column so that the injection tube 5 of the second column is not employed. Because the sample, after passing through the first column, is already diluted in a large volume, the void, if present, in the head of the second column does not become evident or only slightly. If a recycle has to be used, it is suitable to connect a smaller pump, which returns a sample zone back into the injection system, and the operation may be carried out both at the stopped flow of mobile phase and at the flow of mobile phase. Smaller injections (up to 50 ml) may be applied by a syringe, but a small auxiliary pump, pneumatic doser, and the like are more comfortable for larger injections.

Figure 3:
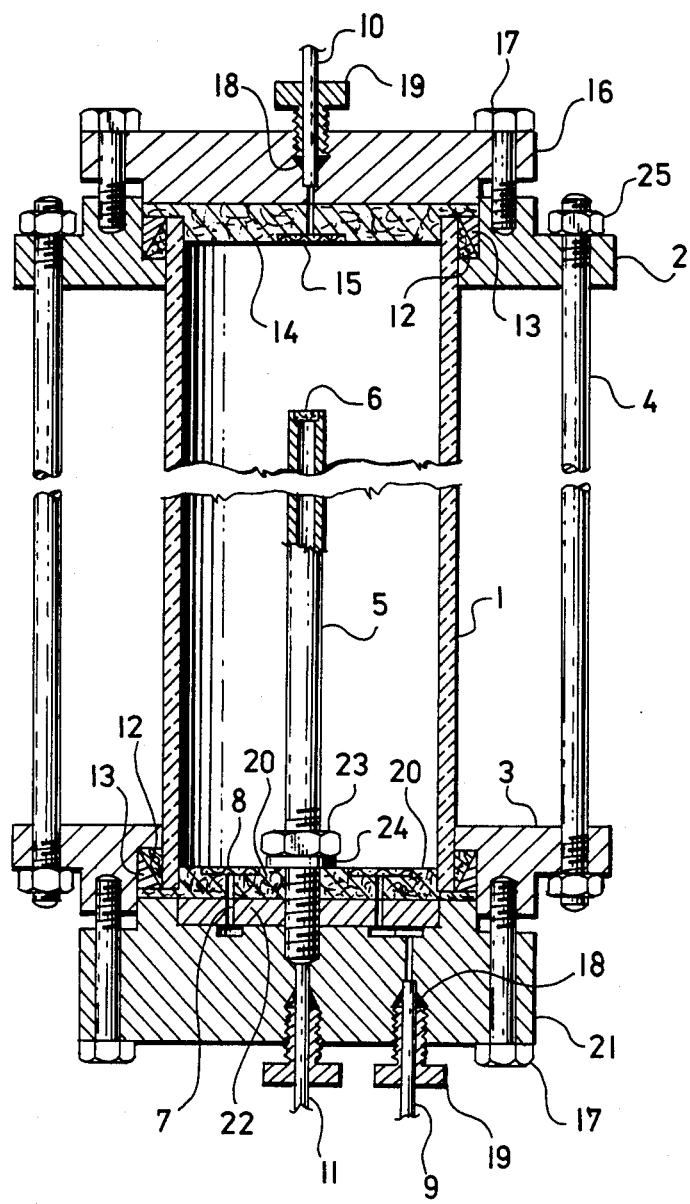
FIG. 3 shows a sectional view of the column according to the example of performance.

A suitable design of the column according to the invention is illustrated in example 1 and shown in FIG. 3.

EXAMPLE 1

A column tube 1 with a length 250 mm, inner diameter 43 mm, and wall thickness 3.5 mm was made from a borosilicate glass (FIG. 3). The upper terminal 2 and the lower terminal 3 were made from stainless steel and the system according to Czechoslovak Pat. No. 236,184 was used for sealing the tube 1. This system consisted of a polytetrafluoroethylene sealing ring 12, stainless-steel sealing ring 13, and polytetrafluoroethylene sealing piece 14 through the centre of which passed an inlet capillary 10 for mobile phase which was separated from a sorbent with a gauze 15. Sealing of the upper terminal 2 was attained by tightening of the lower part of this upper terminal 2 with its upper part 16 by bolts 17. The inlet capillary 10 of mobile phase was sealed with a polytetrafluoroethylene cone 18 and a bored screw 19. Sealing of the tube 1 in the lower terminal 3 was identical with the upper terminal 2, i.e. the polytetrafluoroethylene sealing ring 12 and the stainless-steel sealing ring 13 were used. Four openings 7 were bored in the polytetrafluoroethylene sealing piece 20 in a half of its diameter and covered with gauzes 8. Connecting channels of openingss 7 were formed in the upper part 21 of the lower terminal 3 under a stopper 22 and an outlet capillary 9 of mobile phase was sealed with the polytetrafluoroethylene cone 18 and the bored screw 19. An inlet tube 5 of sample having the inner diameter 1 mm and the inner length 200 mm was furnished with a fritted plate 6 and screwed into the upper part 21 of terminal 3 and the sample inlet was sealed with the polytetrafluoroethylene cone 18 and the screw 19. The inlet tube 5 was tightened from inside with a nut 23 and a washer 24 which both were made from stainless steel. The lower part of the lower terminal 3 and the upper part 21 of this terminal were again tightened with the bolts 17 and sealing of the tube 1 was obtained in this way. The bolts 4 fixing the upper terminal 2 and lower terminal 3 are tightened with nuts 25.

Mobile phase was introduced into the column during operation through the inlet capillary 10 and a sample was injected into a sorbent, after stopping the flow of mobile phase, through the inlet tube 5 for sample to which the inlet capillary 11 for sample was connected. Stopping the flow and injection were carried out by means of a six-way valve which enabled to disconnect the inlet capillary 11 for sample with the dosing equipment for sample. The flow of mobile phase was restored after injection by switching over the six-way valve.

The column according to the invention has a much simpler design that the columns known so far. It may be used for the separation of rare compounds from complex mixtures. The applications comprised above all rare pure compounds for medicine, pharmacy, and also organic syntheses, chemical research, biochemistry and biotechnologies.

We claim:

1. Column for the preparative liquid chromatography which consists of a tube with cylindric shape packed with a sorbent and provided on ends with terminals sealing the column against an inner overpressure in which bolts are attached fixing the terminals on the ends of the said tube, wherein an inlet tube (5) for an injected sample, which is closed at the end with a gauze or fritted plate (6), passes through the centre of the lower terminal (3) and ends in the distance from the lower end of the column equal to 70 to 90% of the total length of the column tube (1), whereas the lower terminal (3) has at least four openings (7) or a circular slot or two half-slots furnished with gauzes or fritted plates (8) and these openings or slots are placed outside the centre of the lower terminal (3) on a concentric circle with diameter ranging between 40 and 70% of the inner diameter of tube (1).

* * * * *